United States Patent [19]

Liss et al.

[11] Patent Number: 4,574,808

[45] Date of Patent: * Mar. 11, 1986

[54] APPARATUS AND METHOD FOR RELIEVING SYMPTOMS OF MULTIPLE SCLEROSIS

[75] Inventors: Saul Liss; Bernard Liss, both of Glen Rock, N.J.

[73] Assignee: Pain Suppression Labs, Inc., Dlmwood Park, N.J.

[*] Notice: The portion of the term of this patent subsequent to Nov. 5, 2002 has been disclaimed.

[21] Appl. No.: 604,139

[22] Filed: Apr. 26, 1984

Related U.S. Application Data

[63] Continuation-in-part of Ser. No. 569,476, Jan. 9, 1984, Pat. No. 4,550,733.

[51] Int. Cl.⁴ ............................................. A61N 1/00
[52] U.S. Cl. .............................................. 128/419 R
[58] Field of Search ..................... 128/419 R, 421–423

[56] References Cited

U.S. PATENT DOCUMENTS

| | | | |
|---|---|---|---|
| 2,004,751 | 6/1935 | Fischler et al. | 128/423 R |
| 3,640,284 | 2/1972 | De Largis | 128/422 |
| 3,791,373 | 2/1974 | Winkler et al. | 128/422 |
| 3,902,502 | 9/1975 | Liss et al. | 128/422 |
| 4,071,033 | 1/1978 | Nawracaj et al. | 128/422 |
| 4,109,660 | 8/1978 | Nesmeyanov et al. | 128/419 R |
| 4,155,366 | 5/1979 | Di Mucci | 128/421 |
| 4,232,680 | 11/1980 | Hudleson et al. | 128/422 |
| 4,305,402 | 12/1981 | Katims | 128/1 C |
| 4,331,145 | 5/1982 | Winter | 128/1 R |
| 4,503,863 | 3/1985 | Katims | 128/421 |

FOREIGN PATENT DOCUMENTS

| | | | |
|---|---|---|---|
| 2500309 | 8/1982 | France | 128/422 |
| 605603 | 5/1978 | U.S.S.R. | 128/421 |

Primary Examiner—William E. Kamm
Assistant Examiner—Mitchell J. Shein
Attorney, Agent, or Firm—Hopgood, Calimafde, Kalil, Blaustein & Judlowe

[57] ABSTRACT

Apparatus and methodology for treating the symptoms of multiple sclerosis employs a transcutaneous electronic wave to suppress perceived pain, increase strength, improve the perception of sensation, reduce spasticity associated with the disease, and create a general feeling of improved well being in the patient. A positive contact electrode is placed on the center of the frontalis muscle, and a negative electrode located at the occiput of the head. Additional negative contacts are placed at the base of the spine, on the medial malleolus of each affected leg and the web space of each affected hand. An electronic current wave comprising relatively high frequency pulses with a low frequency amplitude modulation is then applied between the first to the second electrodes.

6 Claims, 5 Drawing Figures

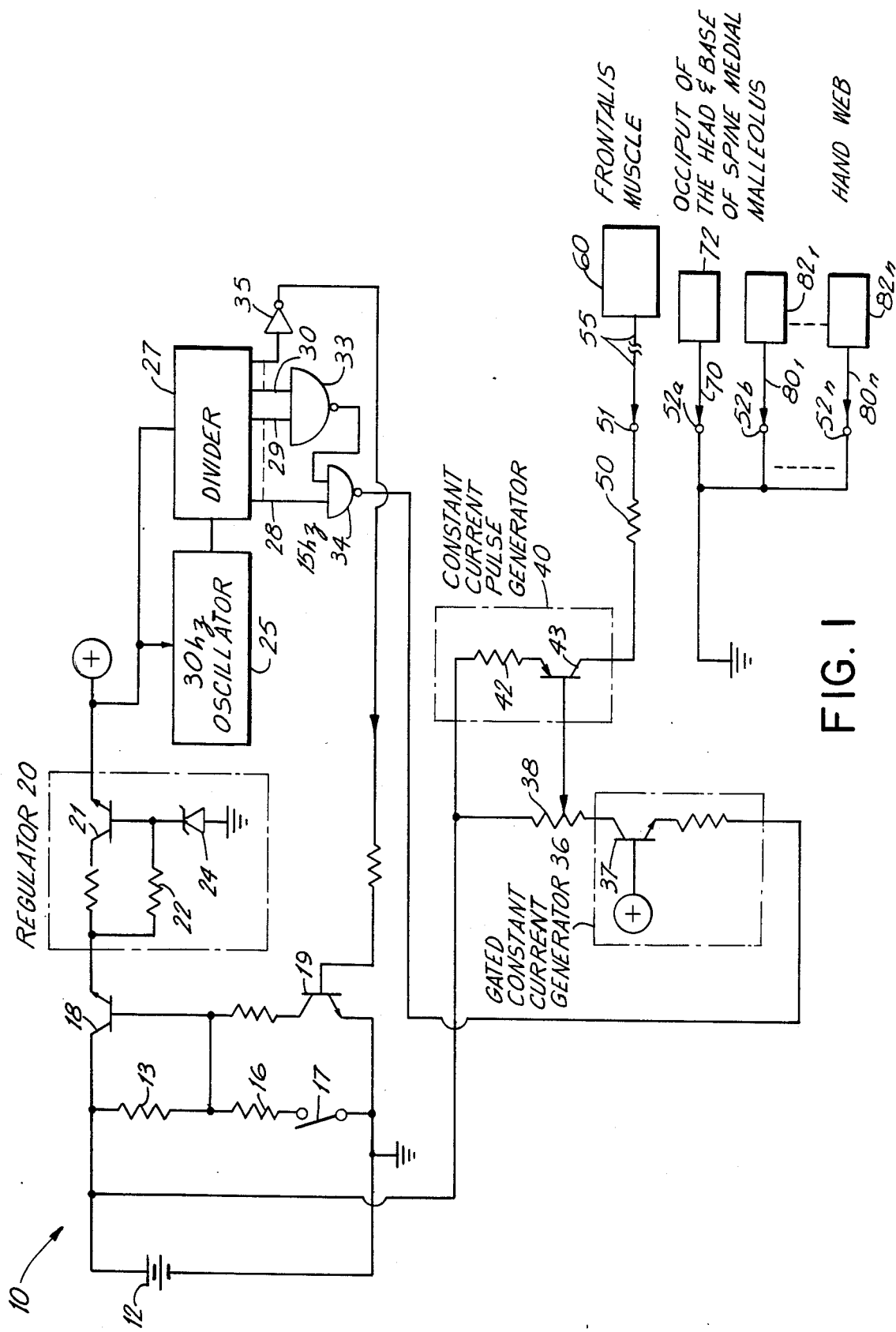
FIG. I

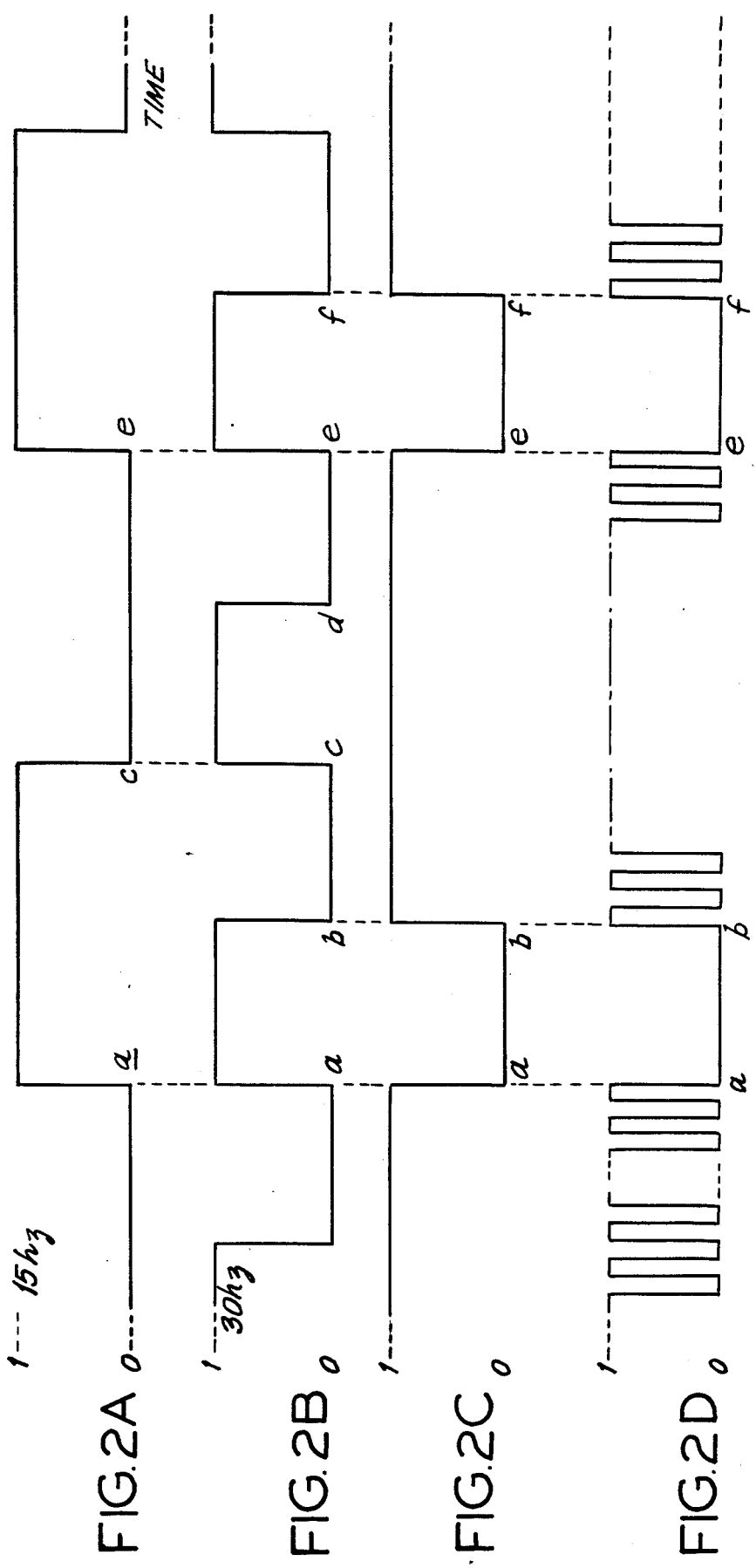

APPARATUS AND METHOD FOR RELIEVING SYMPTOMS OF MULTIPLE SCLEROSIS

This application is a continuation in part of U.S. application Ser. No. 569,476 filed Jan. 9, 1984 now U.S. Pat. No. 4,550,733.

DISCLOSURE OF THE INVENTION

This invention relates to medical electronic apparatus and methodology and, more specifically, apparatus and methodology for relieving symptoms of multiple sclerosis.

It is an object of the present invention to provide improved apparatus and methodology for treating symptoms of multiple sclerosis.

More specifically, an object of the present invention is the electronic treatment of multiple sclerosis symptoms in a safe, efficient and rapid manner to reduce spasticity and alleviate pain associated with the disease, improve perception of sensation, increase strength, and create a general feeling of well being in the patient.

It is a further object of the present invention to provide electronic transcutaneous electronic nerve stimulating equipment operative at very low, milliampere current levels, which relieves perceived pain, and treats all the symptoms of multiple sclerosis.

The above and other objects and features of the instant invention are realized in a specific, illustrative apparatus and methodology for symptomatic treatment of multiple sclerosis which employs a transcutaneous electronic wave to suppress perceived pain, increase strength, improve the perception of sensation, reduce spasticity and to effect a generally improved condition. A positive electrode is placed on the center of the frontalis muscle, and a negative electrode disposed at the occiput of the head. Additional negative contacts are placed at the base of the spine and on the medial malleolus of each affected leg and the web space of each affected hand. An electronic current wave comprising relatively high frequency pulses with a low frequency modulation is then applied from the first to the second electrodes.

The above and other features and advantages of the instant invention will become more clear from the following detailed description of a specific illustrative embodiment thereof, presented hereinbelow in conjunction with the accompanying drawing, in which:

FIG. 1 is a schematic diagram of electronic apparatus for providing symptomatic relief of multiple sclerosis embodying the principles of the present invention; and FIGS. 2A through 2D are wave forms illustrating the operation of the FIG. 1 apparatus.

Multiple sclerosis is a highly variable disease whose cause and pathogenesis are unknown. It is widely believed that immune abnormalities are somehow related to the disease. Three possible mechanisms have been postulated: infection, autoimmunity, and a combination of the two.

Microscopically, the characteristic of multiple sclerosis is the breakdown of the myelin sheath which normally surrounds nerves, with relative sparing of axons. The demyelinating lesions have a perivenous distribution and contain macrophages, lymphocytes, and plasma cells. It is relevant that in most cases of multiple sclerosis, loss of myelin occurs throughout each affected node of Ranvier.

A definite diagnosis of multiple sclerosis requires documentation of lesions that have occurred on more than one occasion and at more than one site and that are not explained by other mechanisms. Electrophysiologic evaluations and computerized tomography used in conjunction with clinical findings are now common in identifying the lesions.

The disease is manifested by sensory, visual and motor dysfunction. Diminution of control and sensory information is exhibited in the extremities and other parts of the body affected thereby. As a result, there is normally a vascular deficiency which alters the normal perceptions in the extremities. Patients normally either feel pins and needles or no sensation at all where sensation would normally be expected. Often reduction in strength and a feeling of cold is manifested.

The apparatus of the instant invention has been found to relieve the symptoms of multiple sclerosis to some degree in all subjects and to produce dramatic results in many patients with a relatively low level current and without chemical intervention.

To illustrate performance of the instant invention in overview, the apparatus of FIG. 1 is utilized to treat the symptoms associated with the diseased state of a patient who is suffering from multiple sclerosis. A positive electrode 60 is secured as by any conventional conductive jell to the center of the frontalis muscle. A negative electrode 72 is placed at the occiput of the head. One or more additional negative contacts 74 and 82 are respectively placed at the base of the spine and on the medial malleolus of each affected leg and on the web space of each affected hand. The treatments should be for 20 minutes and may be run concurrently.

An electronic wave (depicted in FIG. 2D) is applied between the first electrode 60, and the electrodes 72 and 82 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three quarters of the time and off one quarter of the recurring period. For concreteness only and without limitation, it will hereinafter be assumed that the high frequency pulse occurs at a 15 khz rate and 1–1.5 m.a. level, while being subject to a 15 hz modulation with a 3:1 duty factor.

I have found that the wave of FIG. 2D is effective to block the pain perceived and relieve symptoms associated with multiple sclerosis. In a portion of that patient population treated with the present invention, there were dramatic results such as relief from all further attacks, movement where there had been none, and a general feeling of well being. Experience has indicated from such treatment that there can be and has been a reduction in spasticity, a change in the perception of sensation (coldness turning to warmth), an alteration in the amount of strength (improvement), and a greater feeling of positive well being, depending upon the patient. One or more of the above changes in perception or control have been noticed.

The particular mechanism causing elimination of the symptoms is believed to follow from the increase in serotonin produced by the body responsive to the low frequency modulation envelope introduced into the body, with the high frequency wave constituent serving as a transcutaneous carrier for the low frequency modulation.

With respect to reduction in spasticity, it is the result of an imbalance between or among two or more muscle groups which are normally in homeostatic balance but when affected by multiple sclerosis are out of balance, and the hypertonic (stronger) muscle or group overpowers the hypotonic (weaker) muscle or muscle group rehabilitation becomes difficult or impossible. By releasing the hypertonic group of muscles with the use of the high frequency neurological modulator, the hypotonic muscles may be exercised and rehabilitated (make stronger). This allows a person with difficulty in walking to walk more easily, a person unable to exercise, to exercise on behalf of his own rehabilitation, and provides the opportunity for other dysfunctions in the body to tend toward normalization.

While the precise operative mechanisms may be the subject of debate, the fact of the relief of multiple sclerosis symptoms produced by the instant invention is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period (in excess of the time required to complete the procedure) which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass NPN transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and preset. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b–e, —and following time f). Correspondingly, during the periods a–b and e–f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b–e, following the time f, and so forth for the recurring pattern illustrated by FIGS. 2A–2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

The current pulses from generator 40 pass through a protective, series limiting resistor 50 to an output terminal 51. It there flows via the lead 55 connected to terminal 51 to the electrode 60 adhered to the patient's frontalis muscle. The current transcutaneously passes into the patient at the frontalis muscle, flows through the patient, and returns to electronic ground via the electrode pad(s) 72 and 82, respectively disposed at the occiput of the patient's head, spinal base, leg and hand, respectively. Electrodes 72 and 82 are connected to electronic system ground via leads 70 and 80, and apparatus terminal ports 52a and 52b.

As above noted, the apparatus and methodology of the instant invention treats the pain and other symptoms associated with multiple sclerosis. The apparatus and methodology has demonstrated manifest advantages for both the therapist and patient, avoiding the pain, discomfort, spasticity, immobility, weakness, lack of control or sensation, and reversing the depression usually associated with multiple sclerosis.

The above described arrangement and methodology are merely illustrative of the principles of the present invention. Numerous modifications and adaptations thereof will be readily apparent to those skilled in the art without departing from the spirit and scope of the present invention.

What is claimed is:

1. A method for relieving pain an deleterious symptoms associated with multiple sclerosis including the steps of securing a first electrode on the frontalis muscle of a subject's head, securing a second electrode to the occiput of the patient's head, and supplying an electrical wave comprising a high frequency electrical wave bearing a low frequency amplitude modulation to said first and said electrodes.

2. The method as in claim 1, wherein the frequency of said high frequency electrical wave was in the range 12–20 khz, wherein said low frequency modulation is in the range 8–20 hz, and wherein said wave does not exceed about 4 milliamperes.

3. The method as in claim 1 or 2, wherein said amplitude modulation is non-symmetrical.

4. The method as in claim 1 or 2, further comprising the steps of securing a third electrode, electrically connected in common with said second electrode, to the medial malleolus of the patient's leg.

5. The method as in claim 1 or 2, further comprising the steps of securing an electrode, electrically connected in common with said second electrode, to the web of the subject's hand.

6. The method as in claim 4, further comprising the steps of securing an electrode, electrically connected in common with said second electrode, to the web of the subject's hand.

* * * * *

UNITED STATES PATENT AND TRADEMARK OFFICE
CERTIFICATE OF CORRECTION

PATENT NO. : 4,574,808
DATED : March 11, 1986
INVENTOR(S) : Saul Liss, et al.

It is certified that error appears in the above—identified patent and that said Letters Patent is hereby corrected as shown below:

Page 1, [73] Assignee: Pain Suppression Labs, Inc.,
              Dlmwood Park, N.J.

change "Dlmwood Park, N.J." to

--Elmwood Park, N.J.--

Column 5, line 24, change "an" to -- and --.

Signed and Sealed this

Seventeenth Day of June 1986

[SEAL]

Attest:

DONALD J. QUIGG

Attesting Officer

Commissioner of Patents and Trademarks